United States Patent [19]

Tomic

[11] 4,277,463
[45] Jul. 7, 1981

[54] REMEDY PRODUCING HEMOSTATIC AND ANTIPHLOGISTIC EFFECTS

[76] Inventor: Dobrivoje Tomic, 64 McLean St., Wellesly Hills, Mass. 02181

[21] Appl. No.: 62,802

[22] Filed: Aug. 1, 1979

[30] Foreign Application Priority Data

Aug. 4, 1978 [DE] Fed. Rep. of Germany ....... 2834320

[51] Int. Cl.$^3$ ............................................. A61K 33/42
[52] U.S. Cl. .................................................. 424/128
[58] Field of Search ........................................ 424/128

[56] References Cited

PUBLICATIONS

The Merck Index, Eighth Edition, p. 768 (1968).

*Primary Examiner*—Alan L. Rotman
*Attorney, Agent, or Firm*—Morse, Altman, Oates & Dacey

[57] ABSTRACT

A medical composition is provided for use in the topical treatment of wounds and inflammations of the skin and mucous membrane. The composition is characterized by a low pH valve and high osmotic pressure and produces hemostatic and antiphlogestic effects when applied to the affected area. Ingredients include NaCl, KCl, $Na_2HPO_4.12H_2O$, $MgCl_2.6H_2O$ and $H_2O$.

2 Claims, No Drawings

REMEDY PRODUCING HEMOSTATIC AND ANTIPHLOGISTIC EFFECTS

The invention deals with a substance producing healing, antiphlogistic, and hemostatic effects, which can be applied for the treatment of wounds and illnesses of the soft and hard tissues and which presents the composition characterized in the patent claims.

The foundation for conventional antiphlogistics constitutes usually corticosterois, pyrazolidines, and bacteriostatics such as antibiotics and sulfonamides. Conventional hemostatic agents are based primarily on vasoconstrictors such as adrenalin and noradrenalin, or anticoagulants such as thrombin and fibrinogen, and/or absorbing substances such as oxycellulose and gelatin sponges.

The conventional healing, hemostatic and antiphlogistic agents, however, possess numerous disadvantages. The healing effect often is highly dependent upon the adhering quality of the substances, particularly on skin tissue and on mucosa, for instance. The conventional substance often have the disadvantage that long-term treatment is necessary before success can be achieved and that in cases of long-term treatment often tissue damage and allergies are the results. In the application of bacteriostatics the formation of resistant germ cultures is often favored.

The purpose of the invention is to present a remedy for the treatment of soft and hard tissue, producing healing, antiphlogistic and hemostatic effects, which will quickly achieve outstanding compatibility and excellent adherence and also which can be utilized in the long-term treatment without any concern, this being particularly qualified for wound healing and hemostasis.

The invention is based on a special, discovered composition. It presents a comparatively low pH value and high osmotic pressure. On the basis of the composition of the invented substance, hemostasis and antiphlogistic effects are achieved within the shortest periods of time, mostly within minutes. The pH value is determined by the addition of astringents or acids.

On the basis of the invention, the substance has the consistency similar to an emulsion, a paste, a cream, a salve, or as a solution.

For the manufacture of the invented substance, the incorporation and combining of the individual components is to be performed in a pharmaceutical manner. The manufacture of the substance is based on the listed components, which can eventually be obtained in a pre-mixed form, can be blended pharmaceutically.

The invented substance is exceptional in the treatment of inflammations, hemorrhages, wounds of all kinds, and illness of the skin and mucous membrane.

The following examples are to further illustrate the invention.

EXAMPLE I

| Component | Content (in grams) | Approximate Amount (%) |
|---|---|---|
| NaCl | 6.70 g | 0.7 |
| KCl | 0.17 g | 0.02 |
| $Na_2HPO_4 \cdot 12H_2O$ | 6.12 g | 0.6 |
| $MgCl_2 \cdot 6H_2O$ | 0.17 g | 0.02 |
| $Ca_3(PO_4)_2$ | 60.00 g | 6.0 |
| Pectin | 60.00 g | 6.0 |
| Glycerin | 120.00 g | 12.0 |
| MgO | 2.00 g | 0.2 |
| $H_2O$ | ad 1 l | ad 1000 |

EXAMPLE II

| Component | Content (in grams) | Approximate Amount (%) |
|---|---|---|
| Aluminum acetate-tartrate | 50.00 g | 5.00 |
| NaCl | 7.00 g | 0.70 |
| KCl | 0.17 g | 0.02 |
| $Na_2HPO_4 \cdot 12H_2O$ | 6.00 g | 0.60 |
| $MgCl_2 \cdot 6H_2O$ | 0.17 g | 0.02 |
| $H_2O$ | ad 1 l | ad 100 |

To the Examples I and II a flavor (for example peppermintoil) and/or an astringent (for example tannin, aluminum acetate) or an acid (for example citric acid, phosphoric acid) is/are added depending upon the range of application, as for instance paradentopathies.

I claim:

1. A medicinal composition for use in the topical treatment of wounds and inflammation of the skin and mucous membrane, comprising a pharmaceutically effective mixture of the following ingredients in the following approximate percentage amounts for a 1000 ml preparation thereof, NaCl: 0.7
KCl: 0.02
$Na_2HPO_4.12H_2O$: 0.6
$MgCL_2.6H_2O$: 0.02
$Ca_3(PO_4)_2$: 6.0
Pectin: 6.0
Glycerin: 12.0
MgO: 0.2
$H_2O$: add 1000 ml said composition adapted to produce hemostatic and antiphlogistic effects when applied to the treated area.

2. A medicinal composition for use in the topical treatment of wounds and inflammations of the skin and mucous membrane, comprising a pharmaceutically effective mixture of the following ingredients in the following approximate percentage amounts for a 100 ml preparation thereof, Aluminum acetate-tartrate: 5.0
NaCL: 0.70
KCl: 0.02
$Na_2HPO_4.12H_2O$: 0.60
$Mg CL_2.6H_2O$: 0.02
$H_2O$: add 1000 ml said composition adapted to produce hemostatic and antiphlogistic effects when applied to the treated area.

* * * * *